US008975292B2

(12) United States Patent
Taranta et al.

(10) Patent No.: US 8,975,292 B2
(45) Date of Patent: Mar. 10, 2015

(54) METHOD FOR CONTROLLING ARTHROPODS COMPRISING THE SPOT-WISE APPLICATION OF A GEL

(75) Inventors: Claude Taranta, Stutensee (DE); Tatjana Levy, Mannheim (DE); Ouidad Benlahmar, Mannheim (DE); Marc Nolte, Mannheim (DE); Thomas Kröhl, Schriesheim (DE); Christoph Randt, Mannheim (DE); Thomas Bork, Westhofen (DE); Wolfgang Meier, Limburgerhof (DE); Clark D. Klein, Pittsboro, NC (US); Tiffany Hennessey, Wake Forest, NC (US)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 13/011,094

(22) Filed: Jan. 21, 2011

(65) Prior Publication Data
US 2011/0184040 A1   Jul. 28, 2011

Related U.S. Application Data

(60) Provisional application No. 61/297,294, filed on Jan. 22, 2010.

(51) Int. Cl.
| *A01N 43/36* | (2006.01) |
| *A61K 31/40* | (2006.01) |
| *A01N 37/34* | (2006.01) |
| *A61K 31/275* | (2006.01) |
| *A01N 25/04* | (2006.01) |
| *A01N 25/00* | (2006.01) |
| *A01N 31/02* | (2006.01) |
| *A01N 43/22* | (2006.01) |
| *A01N 47/34* | (2006.01) |
| *A01N 53/00* | (2006.01) |

(52) U.S. Cl.
CPC ........... *A01N 25/04* (2013.01); *A01N 25/00* (2013.01); *A01N 25/006* (2013.01); *A01N 31/02* (2013.01); *A01N 43/22* (2013.01); *A01N 43/36* (2013.01); *A01N 47/34* (2013.01); *A01N 53/00* (2013.01)
USPC ........................ 514/427; 514/521; 514/522

(58) Field of Classification Search
None
See application file for complete search history.

(56) References Cited

U.S. PATENT DOCUMENTS

| 3,954,968 | A | | 5/1976 | McKibben |
| 4,668,455 | A | * | 5/1987 | Hansen et al. ............... 264/143 |
| 5,008,478 | A | | 4/1991 | Bartelt et al. |
| 5,017,620 | A | * | 5/1991 | Grassman et al. ............ 514/698 |
| 5,292,835 | A | | 3/1994 | Jahns et al. |
| 6,224,890 | B1 | * | 5/2001 | Heath et al. .................. 424/409 |
| 8,449,981 | B2 | | 5/2013 | Jung et al. |
| 2003/0198659 | A1 | * | 10/2003 | Hoffmann et al. ............ 424/411 |
| 2007/0213226 | A1 | * | 9/2007 | Sieverding et al. ........... 504/206 |
| 2010/0068525 | A1 | | 3/2010 | Jung et al. |
| 2010/0261839 | A1 | | 10/2010 | Jung |
| 2010/0291022 | A1 | | 11/2010 | Huchet et al. |
| 2013/0225717 | A1 | | 8/2013 | Jung et al. |

FOREIGN PATENT DOCUMENTS

| DE | 199 45 846 | 3/2001 |
| DE | 102004054960 | 5/2006 |
| DE | 102007055813 | 6/2008 |
| EP | 0 141 584 | 5/1985 |
| EP | 0457154 | 11/1991 |
| EP | 0547828 | 6/1993 |
| EP | 1 447 003 | 8/2004 |
| GB | 2 445 179 | 7/2008 |
| WO | WO 98/44912 | 10/1998 |
| WO | WO 98/45036 | 10/1998 |
| WO | WO 99/13724 | 3/1999 |
| WO | WO 00/48465 | 8/2000 |
| WO | WO 2008/031870 | 3/2008 |
| WO | WO 2008/071649 | 6/2008 |
| WO | WO 2012/095444 | 7/2012 |

OTHER PUBLICATIONS

Pinero, Jaime, C., et al., "Field evaluation of plant odor and pheromonal combinations for attracting plum curculios", Journal of Chemical Ecology, 2003, p. 2735-2748, vol. 29, No. 12.
Trona, Federica, et al., "Coding and interaction of sex pheromone and plant volatile signals in the antennal lobe of the codling moth *Cydia pomonella*", The Journal of Experimental Biology, 2010, p. 4291-4303, vol. 213.
Yang, Zhihua, et al., "Host plant volatiles synergize response to sex pheromone in codling moth *Cydia pomonella*", Journal of Chemical Ecology, 2004, p. 619-629, vol. 30, No. 3.
International Search Report, issued in PCT/EP2011/050579, dated May 6, 2011.

* cited by examiner

*Primary Examiner* — Wu-Cheng Winston Shen
*Assistant Examiner* — Jared D Barsky
(74) *Attorney, Agent, or Firm* — Brinks Gilson & Lione

(57) ABSTRACT

The present invention relates to a method for controlling arthropods comprising the application of an aqueous gel which contains an insecticide, an attractant and a thickener, wherein the aqueous gel is applied in the form of spots on fruit trees. The invention further relates to an aqueous gel comprising an insecticide, an attractant, a thickener, a humectant and a feeding stimulant. The invention also relates to a concentrated gel for preparing the aqueous gel.

18 Claims, No Drawings

METHOD FOR CONTROLLING ARTHROPODS COMPRISING THE SPOT-WISE APPLICATION OF A GEL

U.S. PROVISIONAL BENEFIT

This application claims the benefit of U.S. Provisional Application No. 61/297,294, filed Jan. 22, 2010, the entire contents of which is hereby incorporated herein by reference.

The present invention relates to a method for controlling arthropods comprising the application of a aqueous gel which contains an insecticide, an attractant and a thickener, wherein the aqueous gel is applied in the form of spots on plants or a solid article. The invention further relates to a aqueous gel comprising an insecticide, an attractant, a thickener, a humectant and a feeding stimulant. The invention also relates to a concentrated gel for preparing the aqueous gel. Combinations of preferred embodiments with other preferred embodiments are within the scope of the present invention.

Various methods for controlling insects, especially flying insects, are known:

EP 0 547 828 discloses a device for control of flying insects comprising means for trapping flying insects and a water-releasing aqueous gel. The gel may comprise a pheromone, a thickener or an attractant.

U.S. Pat. No. 3,954,968 discloses a gelled emulsion for attracting the boll weevil comprising an attractant, glycerol, thickener, preservative and water. The gel was poured in cups and offered to the insects.

WO 2008/031870 discloses a method for combating arthropod pests, comprising applying a composition to a location where the pest contacts the composition. The composition may be applied to parts of plants to be protected. The composition may be a gel, which contains a pesticide, a superabsorbent polymer, a filler material (e.g. an attractant, or a feed stimulant) and water.

Object of the present invention was find an improved method for controlling insects.

The object was solved by a method for controlling arthropods comprising the application of a aqueous gel which contains an insecticide, an attractant and a thickener, wherein the aqueous gel is applied in the form of spots on plants or a solid article.

Prior to application a concentrated gel is preferably diluted with a liquid, such as water, giving the aqueous gel. In a further preferred embodiment, the aqueous gel is a diluted gel. Usually, the aqueous gel is prepared by mixing the concentrated gel and water in a weight ratio concentrated gel/water from 3/1 to 1/10, preferably from 2/1 to 1/5, more preferably from 1/1 to 1/3. The concentrated gel and the aqueous gel usually only differ in the concentration of water.

The aqueous and the concentrated gel refer to formulations that have a higher dynamic viscosity η than water (η of water is 1.0 mPa·s at 20° C.) and are not a solids. The rheology of the aqueous and the concentrated gel is usually comparable to ketchup or toothpaste at 20° C. More preferably, the aqueous gel and the concentrated gel are viscoelastic gels. The gel like state is usually found in a temperature range from −10 to 54° C., preferably from 1 to 45° C.

Typically, the aqueous gel behaves rheologically like a viscoelastic material. The dynamic viscosity η of the aqueous gel is usually in the range of from 30 to 10.000 mPa·s, more preferably from 50 to 1000 mPa·s and especially from 80 to 500 mPa·s (determined by rotational viscosimetry at 20° C., shear rate 100 s$^{-1}$)

The aqueous gel usually behaves like an elastic gel at low shear stress whereas being a low-viscous liquid at high shear stress. "Liquid"-like behaviour is often required for good sprayability whereas the "stiffer" elastic state is usually needed for good adhesiveness on the target surface. Further information on the rheological behaviour at low and high shear conditions can be obtained by steady state flow experiments, yielding the two rheological parameters zero-shear viscosity $\eta_0$ at "zero" shear stress and infinite-shear viscosity $\eta_\infty$ at "infinite" shear stress. The zero-shear viscosity $\eta_0$ of the aqueous gel should be "high" for good adhesiveness on the target surface in order to achieve a low run-off. Thus, the zero-shear viscosity $\eta_0$ of the aqueous gel is preferably at least 100 Pa·s and more preferably at least 200 Pa·s. On the other hand, the infinite-shear viscosity $\eta_\infty$ of the aqueous gel should be "low" for good sprayability. Thus, the aqueous gel has an infinite-shear viscosity $\eta_\infty$ preferably below 300 mPa·s, more preferably below 200 mPa·s, and most preferably below 100 mPa·s.

From oscillatory rheological testing valuable information for the texture and application property assessment can be obtained by monitoring the rheological parameter Complex modules G* ("stiffness"), being a measure of the at-rest resistance to deformation. Typically, the aqueous gel has a stiffness G* preferably in the range from 1 to 200 Pa, more preferably from 5 to 100 Pa, and most preferably from 10 to 50 Pa. The stiffness is usually determined at 20° C.

As mentioned above, the aqueous gel may be prepared from a concentrated gel by dilution with water. The dynamic viscosity η of the concentrated gel is usually in the range from 100 to 100,000 mPa·s, more preferably from 300 to 20,000 mPa·s and especially from 400 to 5000 mPa·s (determined by rotational viscosimetry at 20° C., shear rate 100 s$^{-1}$). For comparison, usual pesticide formulations like suspensions have a dynamic viscosity of about 100 mPa·s under these analytical conditions. Typically, the concentrated gel has a stiffness G* in the range from 200 to 10,000 Pa, more preferably from 300 to 2000, and most preferably from 400 to 1000 Pa.

The concentrated gel is preferably an aqueous gel. It comprises preferably at least 10 wt % water. More preferably, the aqueous gel comprises 20 to 95 wt % water, even more preferably 40 to 90 wt % and most preferably 50 to 80 wt %.

It is an advantage of the invention, that only parts of the plants (such as the trunk or the foliage) need to be treated with the formulation. Preferably, the aqueous gel is applied to less than 30% of the total surface of the plants, more preferably less than 15%, especially preferably to less than 5%, and most preferably to less than 1%.

The aqueous gel is applied in the form of spots on plants or a solid article. The number of spots per plant is up to 5, preferably up to 2 and more preferably only one. For example, usually a fruit tree requires only one or two spots, preferably only one spot, for an effective treatment. Typically, a spot covers an area of from 1 cm$^2$ to 1000 cm$^2$, more preferably from 10 to 100 cm$^2$. The area of a spot depends on the size of the plants, and usually the aqueous gel is applied to larger plants in the form of larger spots. The spots may have a shape of a circle, a line (e.g. horizontal, vertical or with a slope) or any irregular shape, such as a shape of a wave.

The aqueous gel may be applied by conventional means. Preferably, the aqueous gel is applied by spraying, e.g. as a jet on a spot or as a line. This may be achieved using a conic nozzle without a baffle plate, a solid stream nozzle or a plate with a hole. The pressure is adjusted to apply the desired volume with the orifice of the nozzle. A typical orifice diameter is from 0.1 to 5 mm, more preferably from 0.5 to 1.5 mm most preferably from 0.6 to 0.8 mm with a typical pressure from 0.1 to 8 bar, more preferably from 1 to 5 bar, and most preferably from 2 to 3 bar. The concentrated gel is usually not sprayable, such as under the aforementioned spraying conditions.

The application is not necessarily continuous but preferably shot wise. Each shot has usually from 1 to 200 ml volume, more preferably from 2 to 50 ml, and most preferably from 3 to 20 ml. These amounts per shot are especially suitable for one fruit tree.

Preferably, the application rate is up to 20 l of aqueous gel per hectare of a field on which the plants grow. More preferably, the application rate is up to 10 l/ha, even more preferably up to 5 l/ha and especially up to 3 l/ha. Usually, at least 1 l/ha is recommended. In case the aqueous gel was aqueous with water, the aforementioned application rate relates to the amount of the aqueous gel.

The application may be done repeatedly. Usually, the treatment is effective for several weeks. Thus, the application may be repeated at the earliest after one week, preferably two weeks and more preferably three weeks.

Usually, the aqueous gel is applied in the form of spots on plants or a solid article. Suitable plants are any kind of crop plants or shrubs. Preferably, the plants are fruit trees, such as apple trees, peach trees, citrus trees, olive trees, cherry trees, pear trees. Kaki trees are also examples for fruit trees. Suitable solid articles are panels or boards (e.g. made of plastic, paper or wood), which may be hung up in areas there the pests may be located. Further solid articles are any solid surfaces in a greenhouse. Preferably, the aqueous gel is applied in the form of spots on plants, more preferably on fruit trees.

Depending on the type of insecticide, the method can be used for controlling a large number of arthropods, including insects and arachnids. The method is particularly useful for combating insects, e.g. from the following orders:

lepidopterans (Lepidoptera), for example *Agrotis ypsilon, Agrotis segetum, Alabama argillacea, Anticarsia gemmatalis, Argyresthia conjugella, Autographa gamma, Bupalus piniarius, Cacoecia murinana, Capua reticulana, Chematobia brumata, Choristoneura fumiferana, Choristoneura occidentalis, Cirphis unipuncta, Cydia pomonella, Dendrolimus pini, Diaphania nitidalis, Diatraea grandiosella, Earias insulana, Elasmopalpus lignosellus, Eupoecilia ambiguella, Evetria bouliana, Feltia subterranea, Galleria mellonella, Grapholitha funebrana, Grapholitha molesta, Heliothis armigera, Heliothis virescens, Heliothis zea, Hellula undalis, Hibernia defoliaria, Hyphantria cunea, Hyponomeuta malinellus, Keiferia lycopersicella, Lambdina fiscellaria, Laphygma exigua, Leucoptera coffeella, Leucoptera scitella, Lithocolletis blancardella, Lobesia botrana, Loxostege sticticalis, Lymantria dispar, Lymantria monacha, Lyonetia clerkella, Malacosoma neustria, Mamestra brassicae, Orgyia pseudotsugata, Ostrinia nubilalis, Panolis flammea, Pectinophora gossypiella, Peridroma saucia, Phalera bucephala, Phthorimaea operculella, Phyllocnistis citrella, Pieris brassicae, Plathypena scabra, Plutella xylostella, Pseudoplusia includens, Rhyacionia frustrana, Scrobipalpula absoluta, Sitotroga cerealella, Sparganothis pilleriana, Spodoptera frugiperda, Spodoptera littoralis, Spodoptera litura, Thaumatopoea pityocampa, Tortrix viridana, Trichoplusiani* and *Zeiraphera canadensis;* beetles (Coleoptera), for example *Agrilus sinuatus, Agriotes lineatus, Agriotes obscurus, Amphimallus solstitialis, Anisandrus dispar, Anthonomus grandis, Anthonomus pomorum, Aphthona euphoridae, Athous haemorrhoidalis, Atomaria linearis, Blastophagus piniperda, Blitophaga undata, Bruchus rufimanus, Bruchus pisorum, Bruchus lentis, Byctiscus betulae, Cassida nebulosa, Cerotoma trifurcata, Cetonia aurata, Ceuthorrhynchus assimilis, Ceuthorrhynchus napi, Chaetocnema tibialis, Conoderus vespertinus, Crioceris asparagi, Ctenicera* ssp., *Diabrotica longicornis, Diabrotica semipunctata, Diabrotica* 12-punctata *Diabrotica speciosa, Diabrotica virgifera, Epilachna varivestis, Epitrix hirtipennis, Eutinobothrus brasiliensis, Hylobius abietis, Hypera brunneipennis, Hypera postica, Ips typographus, Lema bilineata, Lema melanopus, Leptinotarsa decemlineata, Limonius californicus, Lissorhoptrus oryzophilus, Melanotus communis, Meligethes aeneus, Melolontha hippocastani, Melolontha melolontha, Oulema oryzae, Otiorrhynchus sulcatus, Otiorrhynchus ovatus, Phaedon cochleariae, Phyllobius pyri, Phyllotreta chrysocephala, Phyllophaga* sp., *Phyllopertha horticola, Phyllotreta nemorum, Phyllotreta striolata, Popillia japonica, Sitona lineatus* and *Sitophilus granaria;* flies, mosquitoes (Diptera), e.g. *Aedes aegypti, Aedes albopictus, Aedes vexans, Anastrepha ludens, Anopheles maculipennis, Anopheles crucians, Anopheles albimanus, Anopheles gambiae, Anopheles freeborni, Anopheles leucosphyrus, Anopheles minimus, Anopheles quadrimaculatus, bactrocera olea, Calliphora vicina, Ceratitis capitata, Chrysomya bezziana, Chrysomya hominivorax, Chrysomya macellaria, Chrysops discalis, Chrysops silacea, Chrysops atlanticus, Cochliomyia hominivorax, Contarinia sorghicola Cordylobia anthropophaga, Culicoides furens, Culex pipiens, Culex nigripalpus, Culex quinquefasciatus, Culex tarsalis, Culiseta inornata, Culiseta melanura, Dacus cucurbitae, Dacus oleae, Dasineura brassicae, Delia antique, Delia coarctata, Delia platura, Delia radicum, Dermatobia hominis, Fannia canicularis, Geomyza Tripunctata, Gasterophilus intestinalis, Glossina morsitans, Glossina palpalis, Glossina fuscipes, Glossina tachinoides, Haematobia irritans, Haplodiplosis equestris, Hippelates* spp., *Hylemyia platura, Hypoderma lineata, Leptoconops torrens, Liriomyza sativae, Liriomyza trifolii, Lucilia caprina, Lucilia cuprina, Lucilia sericata, Lycoria pectoralis, Mansonia titillanus, Mayetiola destructor, Musca domestica, Muscina stabulans, Oestrus ovis, Opomyza florum, Oscinella frit, Pegomya hysocyami, Phorbia antiqua, Phorbia brassicae, Phorbia coarctata, Phlebotomus argentipes, Psorophora columbiae, Psila rosae, Psorophora discolor, Prosimulium mixtum, Rhagoletis cerasi, Rhagoletis pomonella, Sarcophaga haemorrhoidalis, Sarcophaga* sp., *Simulium vittatum, Stomoxys calcitrans, Tabanus bovinus, Tabanus atratus, Tabanus lineola,* and *Tabanus similis, Tipula oleracea,* and *Tipula paludosa;* cockroaches (Blattodea), e.g. *Blattella germanica, Blattella asahinae, Periplaneta americana, Periplaneta japonica, Periplaneta brunnea, Periplaneta fuligginosa, Periplaneta australasiae,* and *Blatta orientalis;* ants, bees, wasps, sawflies (Hymenoptera), e.g. *Athalia rosae, Atta cephalotes, Atta capiguara, Atta cephalotes, Atta laevigata, Atta robusta, Atta sexdens, Atta texana, Crematogaster* spp., *Hoplocampa minuta, Hoplocampa testudinea, Monomorium pharaonis, Solenopsis geminata, Solenopsis invicta, Solenopsis richteri, Solenopsis xyloni, Pogonomyrmex barbatus, Pogonomyrmex californicus, Pheidole megacephala, Dasymutilla occidentalis, Bombus* spp. *Vespula squamosa, Paravespula vulgaris, Paravespula pennsylvanica, Paravespula germanica, Dolichovespula maculata, Vespa crabro, Polistes rubiginosa, Camponotus floridanus,* and *Linepithema humile;* crickets, grasshoppers, locusts (Orthoptera), e.g. *Acheta domestica, Gryllotalpa gryllotalpa, Locusta migratoria, Melanoplus bivittatus, Melanoplus femurrubrum, Melanoplus mexicanus, Melanoplus sanguinipes, Melanoplus spretus, Nomadacris septemfasciata, Schistocerca americana, Schistocerca gregaria, Dociostaurus maroccanus, Tachy-*

*cines asynamorus, Oedaleus senegalensis, Zonozerus variegatus, Hieroglyphus daganensis, Kraussaria angulifera, Calliptamus italicus, Chortoicetes terminifera*, and *Locustana pardalina*.

Preferred arthropods are Lepidoptera, beetles, flies, mosquitoes, cockroaches, ants, bees, wasps, sawflies, crickets, grasshoppers and locusts. In a further embodiment, arthropods are Lepidoptera, beetles, cockroaches, ants, bees, wasps, sawflies, crickets, grasshoppers and locusts. More preferably, the arthropods are Lepidoptera, such as *Cydia pomonella* (codling moth).

The term insecticide refers to at least one active substance selected from the group of the insecticides and nematicides. The skilled worker is familiar with such insecticides, which can be found, for example, in the Pesticide Manual, 14th Ed. (2006), The British Crop Protection Council, London. Suitable insecticides are:

organo(thio)phosphates: acephate, azamethiphos, azinphos-methyl, chlorpyrifos, chlorpyrifos-methyl, chlorfenvinphos, diazinon, dichlorvos, dicrotophos, dimethoate, disulfoton, ethion, fenitrothion, fenthion, isoxathion, malathion, methamidophos, methidathion, methyl-parathion, mevinphos, monocrotophos, oxydemeton-methyl, paraoxon, parathion, phenthoate, phosalone, phosmet, phosphamidon, phorate, phoxim, pirimiphos-methyl, profenofos, prothiofos, sulprophos, tetrachlorvinphos, terbufos, triazophos, trichlorfon;

carbamates: alanycarb, aldicarb, bendiocarb, benfuracarb, carbaryl, carbofuran, carbosulfan, fenoxycarb, furathiocarb, methiocarb, methomyl, oxamyl, pirimicarb, propoxur, thiodicarb, triazamate;

pyrethroids: allethrin, bifenthrin, cyfluthrin, cyhalothrin, cyphenothrin, cypermethrin, alpha-cypermethrin, beta-cypermethrin, zeta-cypermethrin, deltamethrin, esfenvalerate, etofenprox, fenpropathrin, fenvalerate, imiprothrin, lambda-cyhalothrin, permethrin, prallethrin, pyrethrin I and II, resmethrin, silafluofen, tau-fluvalinate, tefluthrin, tetramethrin, tralomethrin, transfluthrin, profluthrin, dimefluthrin;

insect growth regulators: a) chitin synthesis inhibitors: benzoylureas: chlorfluazuron, cyramazin, diflubenzuron, flucycloxuron, flufenoxuron, hexaflumuron, lufenuron, novaluron, teflubenzuron, triflumuron; buprofezin, diofenolan, hexythiazox, etoxazole, clofentazine; b) ecdysone antagonists: halofenozide, methoxyfenozide, tebufenozide, azadirachtin; c) juvenoids: pyriproxyfen, methoprene, fenoxycarb; d) lipid biosynthesis inhibitors: spirodiclofen, spiromesifen, spirotetramat;

nicotinic receptor agonists/antagonists compounds: clothianidin, dinotefuran, imidacloprid, thiamethoxam, nitenpyram, acetamiprid, thiacloprid, 1-(2-chloro-thiazol-5-ylmethyl)-2-nitrimino-3,5-dimethyl-[1,3,5]triazinane;

GABA antagonist compounds: endosulfan, ethiprole, fipronil, vaniliprole, pyrafluprole, pyriprole, 5-amino-1-(2,6-dichloro-4-methyl-phenyl)-4-sulfinamoyl-1H-pyrazole-3-carbothioic acid amide;

macrocyclic lactone insecticides: abamectin, emamectin, milbemectin, lepimectin, spinosad, spinetoram;

mitochondrial electron transport inhibitor (METI) I acaricides: fenazaquin, pyridaben, tebufenpyrad, tolfenpyrad, flufenerim;

METI II and III compounds: acequinocyl, fluacyprim, hydramethylnon;

Uncouplers: chlorfenapyr;

oxidative phosphorylation inhibitors: cyhexatin, diafenthiuron, fenbutatin oxide, propargite;

moulting disruptor compounds: cryomazine;

mixed function oxidase inhibitors: piperonyl butoxide;

sodium channel blockers: indoxacarb, metaflumizone;

others: benclothiaz, bifenazate, cartap, flonicamid, pyridalyl, pymetrozine, sulfur, thiocyclam, flubendiamide, chlorantraniliprole, cyazypyr (HGW86), cyenopyrafen, flupyrazofos, cyflumetofen, amidoflumet, imicyafos, bistrifluoron, and pyrifluquinazon.

Preferred insecticides are pyrethroids, sodium channel blockers, and/or uncouplers. More preferred insecticides are alpha-cypermethrin, metaflumizone and/or chlorfenapyr. The insecticide may be present in any form, such as dissolved, emulsified, suspended or encapsulated. Preferably it the insecticide is suspended or encapsulated.

The concentration of the insecticide strongly depends on its insecticidal activity against the insects. Thus, an expert will select an appropriate concentration based on the insecticidal activity and official regulations of national offices. For example, the concentrated gel comprises 0.01 to 30 wt % insecticide, more preferably 0.1 to 10 wt %. For example, the aqueous gel comprises 0.001 to 15 wt % insecticide, more preferably 0.01 to 8 wt %.

Attractants are non-pesticidal materials which may act in one or several of the following ways: a) entice the insect to approach the composition or the material treated with the composition; b) entice the insect to touch the composition or the material treated with the composition; c) entice the insect to consume the composition or the material treated with the composition; and d) entice the insect to return to the composition or the material treated with the composition. Suitable attractants include non-food attractants and food attractants, also termed as feeding stimulants.

The attractants can be included in any form, such as solid or liquid form. It is also possible to include encapsulated attractants. Various known encapsulation techniques may be used for encapsulation of the attractants, such as the semiochemicals. For example EP 0141584 discloses microcapsules wherein the shell contains a polymer (e.g. polymethylmethacrylates) and the core an biologically active (e.g. codlure); or WO 98/45036 discloses microcapsules with a polyurea or polyurethane shell, wherein a pheromone (e.g. codlemone) is encapsulated. Typically, the capsule shell comprises a poly(meth)acrylate or a polyurethane, wherein poly (meth)acrylate is preferred.

Poly(meth)acrylate is a known encapsulation material, for example from WO 2008/071649, EP 0 457154 or DE 10 2007 055 813. Usually, the poly(meth)acrylate comprises $C_1$-$C_{24}$ alkyl esters of acrylic and/or methacrylic acid, acrylic acid, methacrylic acid, and/or maleic acid in polymerized form. More preferably, the poly(meth)acrylate comprises methyl methacrylate and methacrylic acid. The poly(meth)acrylate may also comprise in polymerized form one or more difunctional or polyfunctional monomers. The poly(meth)acrylate may further comprise other monomers.

More preferably, the poly(meth)acrylate polymer is synthesized from 30 to 100 wt %, based on the total weight of the monomers, of one or more monomers (monomers I) from the group comprising $C_1$-$C_{24}$ alkyl esters of acrylic and/or methacrylic acid, acrylic acid, methacrylic acid, and maleic acid, 10 to 70 wt %, based on the total weight of the monomers, of one or more difunctional or polyfunctional monomers (monomers II), and 0 to 40 wt %, based on the total weight of the monomers, of one or more other monomers (monomers III).

Capsules with encapsulation material comprising a polyurethane are well known and can be prepared by analogy to prior art. They are preferably prepared by an interfacial polymerization process of a suitable polymer wall forming material. Interfacial polymerization is usually performed in an aqueous water-in-oil emulsion or suspension of the core material containing dissolved therein at least one part of the polymer wall forming material. During the polymerization, the polymer segregates from the core material to the boundary surface between the core material and water thereby forming the wall of the microcapsule. Thereby an aqueous suspension of the microcapsule material is obtained. Suitable methods for interfacial polymerization processes for preparing microcapsules containing pesticide compounds have been disclosed in prior art, e.g. U.S. Pat. No. 3,577,515, U.S. Pat. No. 4,280,833, U.S. Pat. No. 5,049,182, U.S. Pat. No. 5,229,122, U.S. Pat. No. 5,310,721, U.S. Pat. No. 5,705,174, U.S. Pat. No. 5,910,314, WO 95/13698, WO 00/10392, WO 01/68234, WO 03/099005, EP 619,073 or EP 1,109,450, to which full reference is made.

Suitable wall forming materials for polyurethane capsules include preferably 2- or 3-component systems such as
polyfunctional isocyanate/polyfunctional alcohol,
polyfunctional isocyanate/polyfunctional amine and
polyfunctional isocyanate+polyfunctional acid or acid chloride/polyfunctional amine.

Preferably, the polyurethane comprises polyfunctional isocyanate (also called polyisocyanate) and polyfunctional amine (also called polyamine) in polymerized form.

It is also known, that an isocyanate group may react with water to a carbamic acid group, which in turn may eliminate carbon dioxide to yield finally an amine group.

In a further embodiment, the 2-component system polyfunctional isocyanate/polyfunctional amine may be prepared by reacting the polyfunctional isocyanate with water.

In general, polyurethane is formed by reacting a polyisocyanate, having at least two isocyanate groups with a polyamine having at least two primary amino groups, optionally in the presence of a polyfunctional acid chloride, to form a polyurea wall material. Polyisocyanates may be used individually or as mixtures of two or more Polyisocyanates. Polyisocyanates which are suitable for use include di- and triisocyanates, wherein the isocyanate groups are attached to an aliphatic or cycloaliphatic moiety (aliphatic isocyanates) or to an aromatic moiety (aromatic isocyanates).

Suitable polyamines within the scope of this invention will be understood as meaning in general those compounds that contain two and more amino groups in the molecule, which amino groups may be linked to aliphatic or aromatic moieties. Examples of suitable aliphatic polyamines are $\alpha,\omega$-diamines Suitable non-food attractants are usually volatile material. The volatile attractants act as a lure and their type will depend on the pest to be controlled in a known manner. Non-food attractants include:
semiochemicals such as pheromones, in particular sex pheromones and aggregation pheromones, kairomones and
flavours of natural or synthetic origin.

Suitable semiochemicals can be taken for example from T. D. Wyatt, Pheromones and Animal Behaviour Communication by Smell and Taste, Cambridge 2003: Cambridge University Press. Examples include volatile alkanols and alkenols having from 5 to 10 carbon atoms, volatile alkanols and alkenols having from 5 to 10 carbon atoms, alkanones having from 6 to 10 carbon atoms, 1,7-dioxaspirononan and 3- or 4-hydroxy-1,7-dioxaspiroundecan, benzyl alcohol, Z-(9)-tricosene (muscalure), heneicosene, diacetyl, alcanoic acids having from 5 to 10 carbon atoms such as caprylic acid, laurylic acid, α-pinen, methyleugenol, ethyldodecanoate, tert-butyl 4-(or 5-)chloro-2-ethylcyclohexanecarboxylate, myrcenone, cucurbitacin, trimedlure (commercially available as Capilure®), and (E,E)-8,10-Dodecadien-1-ol (codlemone). In a preferred embodiment, the attractant is a samiochemical, such as a pheromone.

Suitable flavors include meat flavour, yeast flavour, seafood flavour, milk flavour, butter flavour, cheese flavour, onion flavour, and fruit flavours such as flavours of apple, apricot, banana, blackberry, cherry, currant, gooseberry, grape, grapefruit, raspberry and strawberry.

Suitable feeding stimulants include:
proteins, including animal proteins and plant proteins, e.g. in the form meat meal, fish meal, fish extracts, seafood, seafood extracts, or blood meal, insect parts, crickets powder, yeast extracts, egg yolk, protein hydrolysates, yeast autolysates, gluten hydrolysates, and the like;
carbohydrates and hydrogenated carbohydrates, in particular mono- and disaccharides such glucose, arabinose, fructose, mannose, sucrose, lactose, galactose, maltose, maltotriose, maltotetraose, maltopentaose or mixtures thereof such as molasses, corn syrup, maple syrup, invert sugars, and honey; polysaccharides including starch such as potato starch, corn starch, and starch based materials such as cereal powders (e.g. wheat powder, maize powder, malt powder, rice powder, rice bran), pectines, and glycerol, hydrogenated mono- and oligosaccharides (sugar alcohols) such as xylitol, sorbitol, mannitol, isomaltolose, trehalose and maltitol as well as maltitol containing syrups;
fats and oils, such as vegetable oils, e.g. corn oil, olive oil, caraway oil, linseed oil, canola oil, peanut oil, rape seed oil, sesame oil, soy bean oil, sunflower oil, fats and oils of animal origin such as fish based oil, and also fatty acids derived from the aforementioned fats and oils. A further suitable vegetable oil is coconut oil.

The aforementioned attractants may also be present in the form of complex mixtures comprising volatile materials and feeding stimulants such as fruit juices, fruit syrups, and fruit extracts (e.g. apple extracts, which may contain fructose, glucose and fruit acids), decaying parts of organic material such as decaying parts of fruits, crops, plants, animals, insects or specific parts thereof.

The concentration of the attractant strongly depends on its attractant activity for the insects. Thus, an expert will select an appropriate concentration based on the attractant activity. For example, the concentrated gel comprises 0.0001 to 10 wt % attractant, more preferably 0.001 to 1 wt %. For example, the aqueous gel comprises 0.0001 to 5 wt % attractant, more preferably 0.001 to 1 wt %.

Suitable defoamers include polysiloxanes, such as polydimethyl siloxane and waxes. The amount of defoamer will be generally not exceed 1% by weight, based on the total weight of the composition. Typically, the defoamer may be present in the concentrated gel in amounts ranging from 0.001 to 1% by weight, in particular from 0.001 to 0.8% by weight Suitable humectants are glycerol, sorbitol, glucose, fructose, propylenglycol, glucitol, polyethylenglycoles (molecular weight preferably less than 3000 g/mol), sodium lactate, potassium lactate, calcium lactate, maltitol, polydextrose, and invert sugar. Preferably the humectant is glycerol. The amount of humectant will be generally not exceed 50% by weight, based on the total weight of the concentrated gel. Typically, the humectant may be present in the concentrated gel in amounts ranging from 1 to 40% by weight, in particular from 5 to 30% by weight and especially 10 to 25 wt %.

Typically, the humectant may be present in the aqueous gel in amounts ranging from 0.5 to 20% by weight, in particular from 2 to 15% by weight and especially 3 to 10 wt %.

Suitable thickeners include inorganic thickening agents, such as clays, hydrated magnesium silicates and, preferably, organic thickening agents. Suitable organic thickeners are polysaccharide gums (e.g. gellan gum, jelutong gum, xanthan gum, guar gum, gum arabic, gum tragacanth, gum karya, tara gum, locust gum, agar agar, carrageenan, alginic acid, alginates (e.g. sodium, potassium, ammonium, or calcium)), starch and its derivatives, water soluble synthetic polymer thickener (e.g. anionic or neutral copolymers based on vinylalcohol, acrylic acid and its salts, methacrylic acid and its salts, acrylamide, vinylpyrrolidone, styrene and maleic acid anhydride; cationic copolymers, e.g. based on cationic vinylimidazolium monomers), water soluble peptides (such as casein or gelatine), and cellulose derivatives (such as carboxymethyl cellulose, hydroxyethyl cellulose, hydroxypropyl methylcellulose, hydroxypropyl cellulose, ethylhydroxyethyl cellulose). Mixture of any of the aforementioned thickener are also suitable. Among the water soluble synthetic polymer thickeners those are preferred which comprise less than 5 mol %, preferably less than 0.5 mol % of acrylic acid and its salts, or methacrylic acid and its salts.

Preferred thickeners are polysaccharide gums, starch and its derivatives, water soluble peptides, cellulose derivatives, and water soluble synthetic polymer thickener. More preferred thickeners are polysaccharide gums, and cellulose derivatives.

The amount of thickener in the aqueous gel depends on the thickening capabilities of the respective thickener. Thus, an expert will select an appropriate amount of thickener which is required to prepare a aqueous gel. Typically, the concentrated gel comprises up to 15 wt % of thickener. Preferably, the concentrated gel comprises 0.1 to 25 wt % of thickener, more preferably 0.5 to 15 wt % and especially from 1.0 to 10 wt %. Typically, the aqueous gel comprises up to 8 wt % of thickener. Preferably, the aqueous gel comprises 0.01 to 12 wt % of thickener, more preferably 0.1 to 8 wt % and especially from 0.5 to 5 wt %.

In a preferred embodiment the aqueous gel and the concentrated gel contain less than 1 wt % of synthetic polymer thickeners, more preferably less than 0.1 wt %. Especially preferred is a aqueous gel and a concentrated gel which is free of synthetic polymer thickeners.

Suitable preservatives to prevent microbial spoiling of the formulations of the invention include formaldehyde, alkyl esters of p-hydroxybenzoic acid, sodium benzoate, 2-bromo-2-nitropropane-1,3-diol, o-phenylphenol, thiazolinones, such as benzisothiazolinone, 5-chloro-2-methyl-4-isothiazolinone, pentachlorophenol, 2,4-dichloro-benzyl alcohol and mixtures thereof. The amount of preservatives will be generally not exceed 1.0% by weight, based on the total weight of the aqueous and the concentrated gel.

Suitable repellents may be present to avoid uptake by vertebrates such as birds, amphibians, reptiles or warm blooded animals, in particular human beings. Suitable repellents are bitterness agents such as denatonium benzoate (N-benzyl-2-(2,6-dimethyl-phenylamino)-N,N-diethyl-2 oxoethanaminium benzoate) and hot substances such as Guinea pepper.

Suitable UV filters may be chosen from the following groups:

A) benzotriazoles, such as 2-(2H-benzotriazol-2-yl)-4,6-bis(1-methyl-1-phenylethyl)-phenol (Tinuvin® 900, CIBA AG), [3-[3-(2H-benzotriazol-2-yl)-5-(1,1-dimethylethyl)-4-hydroxyphenyl]-1-oxopropyl]-w-[3-[3-(2Hbenzotriazol-2-yl)-5-(1,1-dimethyl-ethyl)-4-hydroxyphenyl]-1-oxopropoxy]poly(oxy-1,2-ethanediyl) (Tinuvin® 1130, CIBA AG), 6-tert.-butyl-2-(5-chloro-2H-benzotriazol-2-yl)-4-methylphenol, 2,4-di-tert-butyl-6-(5-chloro-2H-benzotriazol-2-yl)-phenol, 2-(2H-benzotriazol-2-yl)-4,6-di-tert.-pentylphenol, 2-(2H-benzotriazol-2-yl)-4-(1,1,3,3-tetramethylbutyl)-phenol, 2-(2H-benzotriazol-2-yl)-4-methylphenol, 2-(2H-benzotriazol-2-yl)-4,6-bis(1-methyl-1-phenylethyl)phenol;

B) Cyanoacrylate derivatives, such as ethyl 2-cyano-3-phenylcinnamate (Uvinul® 3035, BASF SE), 2-cyano-3,3-diphenylacrylic acid-2'-ethylhexyl ester or 2-ethyl-hexyl-2-cyano-3-phenylcinnamate (octocrylene, Uvinul® 539 T, Uvinul 3039, BASF SE);

C) para-aminobenzoic acid (PABA) derivatives, especially esters, such as ethyl-PABA, ethoxylated PABA, ethyl-dihydroxypropyl-PABA, Glycerol-PABA, 2-ethyl-hexyl 4-(dimethylamino)benzoate (Uvinul® MC 80), 2-octyl 4-(dimethylamino)-benzoate, amyl 4-(dimethylamino) benzoate, 4-bis(polyethoxy) 4-amino benzoic acid polyethoxyethyl ester (Uvinul® P 25, BASF SE);

D) esters of salicylic acid, such as 2-ethylhexyl salicylate, 4-isopropylbenzyl salicylate, homomethyl salicylate, TEA salicylate (Neo Heliopan® TS, Haarmann and Reimer), dipropyleneglycol salicylate;

E) esters of cinnamic acid, such as 2-ethylhexyl 4-methoxycinnamate (Uvinul® MC 80), octyl-p-methoxycinnamate, propyl 4-methoxycinnamate, isoamyl 4-methoxycinnamate, conoxate, diisopropyl methylcinnamate, etocrylene (Uvinul® N 35, BASF SE);

F) derivatives of benzophenone, such as 2-hydroxy-4-methoxybenzophenone (Uvinul® M 40, BASF SE), 2-hydroxy-4-methoxy-4'-methylbenzophenone, 2,2'-dihydroxy-4-methoxybenzophenone, 2-(4-diethylamino-2-hydroxybenzoyl)-benzoic acid hexylester (Uvinul® A Plus, BASF SE), 4-n-octyloxy-2-hydroxybenzophenone (Uvinul® 3008, BASF SE), 2-hydroxybenzophenone derivatives such as 4-hydroxy-, 4-methoxy-, 4-octyloxy-, 4-decyloxy-, 4-dodecyloxy-, 4-benzyloxy-, 4,2',4'-trihydroxy-, 2'-hydroxy-4,4'-dimethoxy-2-hydroxybenzophenone;

G) sulfonic acid derivatives of benzophenones, such as 2-hydroxy-4-methoxybenzo-phenone-5-sulfonic acid (Uvinul® MS 40, BASF SE) and its salts, 2,2'-dihydroxy-4,4'-dimethoxybenzophenone-5,5'-sulfonic acid and its salts (disodium salt: Uvinul® DS 49, BASF SE);

H) 3-benzylidenecamphor and derivatives thereof, such as 3-(4'-methylbenzylidene)d-1-camphor, benzylidiene camphor sulfonic acid (Mexoryl® SO, Chimex);

I) sulfonic acid derivatives of 3-benzylidenecamphor, such as 4-(2-oxo-3-bornyl-idenemethyl)benzenesulfonic acid and 2-methyl-5-(2-oxo-3-bornylidene)sulfonic acid and salts thereof;

J) esters of benzalmalonic acid, such as 2-ethylhexyl 4-methoxybenzmalonate;

K) triazine derivatives, such as dioctylbutamidotriazone (Uvasorb® HEB, Sigma), 2,4,6-trinanilino-p-(carbo-2'-ethyl-hexyl-1'-oxy)-1,3,5-triazine (Uvinul® T 150, BASF SE), 2-[4-[(2-Hydroxy-3-(2'-ethyl)hexyl)oxy]-2-hydroxyphenyl]-4,6bis(2,4-dimethylphenyl)-1,3,5-triazine (Tinuvin® 405, CIBA AG), anisotriazine (Tinosorb® S, CIBA AG), 2,4,6-tris(diisobutyl 4'-aminobenzalmalonate)-s-triazine;

L) Propane-1,3-diones, such as, 1-(4-tert-butylphenyl)-3-(4'-methoxyphenyl)propane-1,3-dione;

M) 2-phenylbenzimidazole-5-sulfonic acid or 2-phenylbenzimidazole-4-sulfonic acid and alkali metal, alkaline earth metal, ammonium, alkylammonium, alkanolammonium and glucammonium salts thereof;

N) derivatives of benzoylmethane, such as, 1-(4'-tert-butylphenyl)-3-(4'-methoxy-phenyl)propane-1,3-dione, 4-tert-butyl-4'-methoxydibenzoylmethane or 1-phenyl-3-(4'-isopropylphenyl)propane-1,3-dione;

O) Aminohydroxy-substituted derivatives of benzophenones, such as N,N-diethyl-aminohydroxybenzoyl-n-hexylbenzoate; and P) inorganic absorbers e.g. based on ZnO (e.g. Z-Cote® products, BASF SE), $TiO_2$ (e.g. T-Lite™ products, BASF SE) or $CeO_2$; and Q) mixtures of UV filters of groups A) to O), such as a mixture of p-methoxycinnamic acid ethylhexyl ester (65%) and 2-(4-diethylamino-2-hydroxybenzoyl)benzoic acid hexylester (35%) (Uvinul® A Plus B, BASF SE).

Preferred UV filters are derivatives of benzophenone, more preferably 2-hydroxybenzophenone derivatives and especially 4-n-octyloxy-2-hydroxy-benzophenone.

The amount of UV filter in the aqueous gel depends on the UV filtering capabilities of the respective UV filter. Thus, an expert will select an appropriate amount of UV filter which is recommended to achieve a reasonable UV filtering activity. Typically, the concentrated gel comprises up to 15 wt % of UV filter. Preferably, the concentrated gel comprises 0.01 to 15 wt % of UV filter, more preferably 0.1 to 10 wt % and especially from 0.5 to 5 wt %. Typically, the aqueous gel comprises up to 10 wt % of UV filter. Preferably, the aqueous gel comprises 0.01 to 10 wt % of UV filter, more preferably 0.1 to 5 wt % and especially from 0.3 to 3 wt %.

The present invention also relates to a aqueous gel comprising an insecticide, an attractant, a thickener, a humectant and a feeding stimulant. Suitable and preferred rheological parameters, insecticides, attractants, thickeners, humectants and feeding stimulants are as defined above. The feeding stimulant also belongs to the attractants. Thus, the aqueous gel comprises two different attractants, wherein at least one is selected from the feeding stimulants.

Such a aqueous gel is advantageous for the method according to the invention. Preferably, the aqueous gel comprises 0.01 to 20% wt thickener, 0.5 to 30 wt % humectant, and 0.01 to 40 wt % feeding stimulant. More preferably, the aqueous gel comprises 0.05 to 10% wt thickener, 5 to 30 wt % humectant, and 0.5 to 25 wt % feeding stimulant. Even more preferably, the aqueous gel comprises 0.3 to 5% wt thickener, 2 to 10 wt % humectant, and 1 to 15 wt % feeding stimulant.

The present invention further relates to a concentrated gel for preparing the aqueous gel according to the invention by dilution with water in a weight ratio concentrated gel/water in a range from 3/1 to 1/10. Typically, the concentrated gel comprises an insecticide, an attractant, a thickener, a humectant and a feeding stimulant. Preferably, the concentrated gel comprises 0.01 to 25% wt thickener, 1 to 40 wt % humectant, and 0.1 to 50 wt % feeding stimulant. More preferably, the concentrated gel comprises 0.1 to 15% wt thickener, 5 to 30 wt % humectant, and 1 to 30 wt % feeding stimulant. Even more preferably, the concentrated gel comprises 0.5 to 8% wt thickener, 10 to 20 wt % humectant, and 1 to 15 wt % feeding stimulant.

The aqueous gel and the concentrated gel according to the invention may be prepared by usual methods for preparing gels. Usually, the components are mixed under stirring. Typically, a stirring equipment is used which is suitable for stirring viscous composition. The mixing can be achieved at temperature from 50 to 100° C.

Both the method and the aqueous and concentrated gels according to the invention have various advantages: There is less residue due to spot application compared to a broadcast application over most of the plant. There is only low water evaporation and low active dissemination from the applied aqueous gel due to spot application. The attractant allows for very localized application. There is a lower drift due to spot application. The viscous texture of the aqueous gel allows for no drift. There is a water saving due to low volume application rate. There is an increased residual activity of the insecticide due to UV filter. The worker exposure and environmental impact is reduced due to the targeted concept. There is a reduced impact on the beneficial and non-target organisms. The thickeners are biodegradable or of natural origin. The aqueous gel is easy to spray (especially at pressures between 2 and 5 bar) and sticks very well to the surface of the plants (corresponding to a high retention).

The invention is further illustrated but not limited by the following examples.

EXAMPLES

Materials

Rhodigel® easy: Xanthan gum, granulated powder, loss on drying 8-14 wt %, viscosity 1200-1600 mPas (24° C., 1% KCl, Brookfield LVT, 60 rpm, spindle 3); commercially available from Rhodia.

Culminal® MHPC: Methylhydroxypropylcellulose, granulated powder, viscosity 58000-70000 mPas (2% solution), completely soluble in water; commercially available from Hercules Aqualon.

Synergen® Y02: hydrophobically modified copolymer based on acrylamidomethylpropane sulfonic acid (AMPS), neutralized with ammonia, powder, viscosity 35,000-50,000 mPas (1 wt % aqueous solution, Brookfield viscometer, 20 rpm, 20° C.), water content 5 wt %; pH 5-6 (1 wt % aqueous solution); commercially available from Clariant.

Kelcogel® F: Gellan gum, powder, water soluble; commercially available from C. P. Kelco.

Kelcosol® NF: Alginic acid, sodium salt, powder, viscosity 1000-1500 mPas (1% solution), 7-15 wt % loss on drying, pH 6, 4-8 (1% aqueous solution); commercially available from C. P. Kelco.

Genuvisco® CL-123: Carrageenan, powder, water soluble, 10% loss on drying, gel strength 60-85 g (1.4%); commercially available from C. P. Kelco.

Luvigel® Advanced: Polyquaternium-86 (Copolymer of vinylpyrrolidone, vinylimidazole, 3-methyl-1-vinylimidazolium chloride and methacrylic acid; cross-linked; CAS 935522-29-5), powder; commercially available from BASF SE.

Aquasorb® 3500S: Cross linked copolymer of acrylamide and potassium acrylate; dry matter 85-90%; pH 8.1 in water; commercially available from SNF Floerger.

Luviset® Clear: Copolymer of N-vinylpyrrolidone, methacrylamide and N-vinyl imidazole, Mw: 270 000 g/mol, solid content 20%, viscosity 700-2000 mPas (Brookfield, Sp. 4, 20 rpm. 23° C.); commercially available from BASF SE.

Example 1

Preparation of Concentrated Gel 100 g of each concentrated gel was prepared at room temperature by mixing while stirring 16.14 g of a suspension concentrate comprising 60 g/l alphacypermethrin, 5.0 g saccharose (a feeding stimulant), 5.0 g apple extract (a dark brown syrup made from dried and extracted apples, comprises fructose, glucose, sorbitol, and the flavor of apples), 0.2 g preservative, 15.0 g glycerol (a humectant) and water. After these compounds were homogenized 2.0 g 2-hydroxy-4-(octyloxy)benzophenone (a UV filter) and thickener (amounts see table 1) were added while stirring. The final viscosity of the gel was determined at 20° C. at 100 rpm. Any kind of attractant for arthropods could be added to this model gel.

TABLE 1

|   | Amount | Thickener | Viscosity [mPas] |
|---|--------|-----------|------------------|
| A | 2.5 g  | Rhodigel ® easy | 166 |
| B | 3.5 g  | Culminal ® MHPC | 1945 |
| C | 2.0 g  | Synergen ® Y02 | 622 |
| D | 5.0 g  | Kelcogel ® F | 419 |
| E | 2.0 g  | Kelcosol ® NF | 1127 |
| F | 2.0 g  | Genuvisco ® CL-123 | 480 |
| G | 3.0 g  | Luvigel ® Advanced | 710 |

Example 2

Preparation of Concentrated Gel 100 g of each concentrated gel was prepared at room temperature by mixing while stirring 6.2 g of a suspension concentrate comprising 100 g/l alphacypermethrin, 5.0 g saccharose (a feeding stimulant), 10.0 g Buminal® (protein hydrolysate from Bayer Crop Science), 0.2 g preservative, 15.0 g glycerol (a humectant), 5.0 g Capilure® (attractant based on trimedlure, also known as t-Butyl-4 (or 5)-chloro-2-methylcyclohexanecarboxylate, CAS No. 12002-53-8), and water. After these compounds were homogenized 2.0 g 2-hydroxy-4-(octyloxy)benzophenone (a UV filter) and thickener (amounts see Table 2) were added while stirring.

TABLE 2

|   | Thickener | Water absorber |
|---|-----------|----------------|
| A | 1.5 g Culminal ® MHCP | 2.5 g Aquasorb ® 3500S |
| B | 1.0 g Luviset ® Clear | 3.5 g Aquasorb ® 3500S |
| C | 0.9 g Culminal ® MHPC 0.5 g Kelcogel ® F | 2.5 g Aquasorb ® 3500S |

Example 3

Adhesiveness on Leaves

The adhesiveness on leaves of apple trees at various inclination angles was tested with all gels of example 1 (aqueous with 2 parts by weight of water) at room temperature. All gel spots stuck to the leaf at the spray application without sliding or run-off for more than one hour, even if the inclination angle of the leaf surface was 60° or higher.

Example 4

Biological Testing

In a citrus orchard in Spain the control of *Ceratitis capitata* (Mediterranean fruit fly) was tested by evaluating the attractiveness of the gel formulation applied to green glued boards located on citrus trees and by controlling the reduction of the population of *Ceratitis capitata* in the orchard. The orchard was divided into four zones (each about 0.8 ha with about 300 citrus trees). The test was conducted in late August. The usual Ceratitis fly flow was from southeast to northwest. Thus, in each zone an entry trap was installed at the southeast border, and an exit trap was installed at the northwest border. In each zone four green glued panel were installed evenly distributed throughout the zone.

Zone C0: control, without treatment.

Zone C1: control, each tree and the four panels treated with Spintor® CEBO (aqueous formulation containing 0.02 wt % spinosad, sugars, plant proteins and extracts, commercially available from Dow Agrosciences). The total application rate in Zone C1 was 7.5 l/ha aqueous spray mix, which was prepared by diluting Splintor® with water in a ratio of 1:5. Each tree and the panels were treated with about 17.9 ml of spray mix.

Zone A: each tree and the four panels treated with gel. The total application rate in Zone A was 3.0 l/ha aqueous spray mix, which was prepared by diluting the concentrated gel of Example 2C with water in a ratio of 1:3. Each tree and the panels were treated with about 7.2 ml of spray mix and applied in form of an irregular line spot.

Zone B: every second row (i.e. only 50% of the trees in this zone) and the four panels treated with gel. The total application rate in Zone B was 3.0 l/ha aqueous spray mix, which was prepared by diluting the concentrated gel of Example 2C with water in a ratio of 1:3. Each second tree and the panels were treated with about 14.4 ml of spray mix and applied in form of an irregular line spot.

At various days after treatment (DAT) the number of flies captured on the panels and in the entry and the exit traps were counted.

TABLE 3

| Panel evaluation | | | | |
|---|---|---|---|---|
| | C0 [a)] | C1 [a)] | A | B |
| 3 DAT | 5 | 22 | 33 | 29 |
| 7 DAT | 15 | 21 | 43 | 47 |
| 14 DAT | 13 | 43 | 56 | 30 |
| 21 DAT | 5 | 16 | 21 | 14 |
| Total after 21 DAT | 38 | 102 | 153 | 120 |

[a)] comparative, not according to the invention.

TABLE 4

| Difference 21 DAT Entry/Exit traps | | | | |
|---|---|---|---|---|
| | C0 [a)] | C1 [a)] | A | B |
| Entry trap | 405 | 160 | 205 | 115 |
| Exit trap | 133 | 67 | 123 | 35 |
| Difference | 272 | 93 | 82 | 80 |

[a)] comparative, not according to the invention.

In conclusion, there was in general a high population of flies at the beginning of the trials. A good reduction of the fly population in the treated areas was shown by the difference of Entry/Exit traps in Table 4. This was achieved by the high attractiveness of the gel bait according to the invention, which attracted and killed a high number of flies. It was also possible to reduce the number of treated trees by 50% and still to achieve a higher fly reduction compared to market products. This allows a faster treatment of the orchard in a shorter time and with less labor efforts.

Example 5

Preparation of Concentrated Gel Containing Microcapsules

A) Preparation of Microcapsules
Water Phase:

| | |
|---|---|
| 27.36 g | water |
| 45.63 g | polyvinyl alcohol (10% by weight in water, degree of hydrolysis 88%) |
| 0.17 g | of a 2.5% by weight aqueous sodium nitrite solution |

Oil Phase:

| | |
|---|---|
| 23.93 g | Codlemone/ethylisovalerate (weight ratio 1/9) |
| 11.04 g | Caprylic/Capric Triglyceride |
| 2.58 g | MMA |
| 2.58 g | MAA |
| 1.72 g | BDA2 |
| 1.72 g | PETIA |

Feed 1: 0.30 g tert-butyl perpivalate (75%)
Feed 2: 0.47 g 10 wt % aqueous tert-butyl hydroperoxide solution in hydrocarbons
Feed 3: 2.51 g 1 wt % aqueous ascorbic acid solution First, the water phase and the oil phase were produced separately with the above composition. The water phase was initially charged at room temperature. Addition of the oil phase was followed by dispersion with a disperser stirrer at 15 000 rpm for 1 minute. The emulsion formed was then transferred to a 250 ml flask under nitrogen and stirring. Feed 1 was added and the mixture was heated to 70° C. while stirring with an anchor stirrer and kept at 70° C. for one hour. It was then heated to 85° C. and kept at 85° C. for two hours. Feed 2 was added to the microcapsule dispersion formed while stirring. Feed 3 was metered in within 50 minutes, in the course of which the mixture was cooled to room temperature within 60 minutes. The microcapsule dispersion formed possessed a solids content of 37.7% and a mean particle size of 1.8 μm (measured by Fraunhofer diffraction, volume average).

B) Preparation of Gel 100 g of each concentrated gel was prepared at room temperature by mixing while stirring 1.25 g of the capsule suspension from step A), 5.0 g saccharose (a feeding stimulant), 0.2 g preservative, 15.0 g glycerol (a humectant), and water. After these compounds were homogenized 0.2 g 2-hydroxy-4-(octyloxy)benzophenone (a UV filter) and thickener (0.6 g Aquasorb® 3500S, 0.8 g Culminal® MHPC, 0.2 g Kelcogel® F and 0.2 g Genuvisco® CL-123) were added while stirring.

Example 6

Biological Testing of Capsules of Example 5

In an orchard in Germany (late September) two cages were placed, each around one tree. In each cage two delta traps were placed near the tree. One trap was baited with two female codling moths, the second trap was baited with the gel bait according to Example 5B. 40 male codling moths were then released at 11 am into the cage. 24 h later, the number of caught male moths was counted in each trap (1 DAT). The gel bait was left for 14 days in the trap. After ten days, two new female moths were put into the traps, and 40 new codling moths were released into the cage. The number of caught moths was counted four days later (14 DAT). On the same day, further 40 new codling moths were released into the cage. The number of caught moths was counted three days later (17 DAT). The trial results (Table 4) demonstrated the high and long lasting attractiveness of the gel bait.

TABLE 4

Number of caught male moths by a trap (DAT: days after treatment).

| | Trap baited with female moth [a] | Trap baited with gel bait |
|---|---|---|
| 1 DAT | 3 | 16 |
| 14 DAT | 10 | 25 |
| 17 DAT | 2 | 24 |

[a] comparative, not according to the invention.

The invention claimed is:

1. A sprayable aqueous gel comprising an insecticide, an attractant comprising one or more semiochemicals, a thickener comprising a polysaccharide gum and a water soluble synthetic polymer thickener, where the water soluble synthetic polymer thickener is selected from anionic or neutral copolymers based on vinylalcohol, acrylic acid and its salts, methacrylic acid and its salts, acrylamide, vinylpyrrolidone, styrene and maleic acid anhydride, a humectant and a feeding stimulant
   wherein the feeding stimulant comprises a feeding stimulant selected from proteins, and a feeding stimulant selected from a carbohydrate and hydrogenated carbohydrates,
   wherein the insecticide is present in dissolved, emulsified, suspended or encapsulated form, and
   wherein dynamic viscosity n of the gel is in the range from 50 to 1000 mPas.

2. The aqueous gel of claim 1, wherein the aqueous gel has a stiffness G* in the range from 1 to 200 Pa.

3. The aqueous gel of claim 1, wherein the humectant comprises glycerol and the feeding stimulant comprises a sugar.

4. The aqueous gel of claim 1, wherein the insecticide is selected from the group consisting of alphacypermethrin, metaflumizone, chlorfenapyr, and combinations thereof.

5. A concentrated gel for preparing the aqueous gel as defined in claim 1 by dilution with water in a weight ratio of concentrated gel/water in a range from 3/1 to 1/10.

6. A method for controlling arthropods comprising applying the aqueous gel of claim 1 in the form of spots on a fruit tree.

7. The method of claim 6, wherein the humectant comprises glycerol and the feeding stimulant comprises a sugar.

8. The method of claim 6, wherein the insecticide is selected from the group consisting of alphacypermethrin, metaflumizone, chlorfenapyr, and combinations thereof.

9. The method of claim 6, wherein the aqueous gel is applied to less than 30% of the total surface of the fruit tree.

10. The method of claim 6, wherein a spot covers an area of from 1 cm$^2$ to 100 cm$^2$.

11. The method of claim 6, wherein the aqueous gel is applied by spraying.

12. The method of claim 6, wherein the application rate is up to 10 liters of aqueous gel per hectare of a field on which the fruit tree grows.

13. The method of claim 6, wherein the fruit tree is an apple tree, a peach tree, a citrus tree, an olive tree, a cherry tree, a pear tree, or a kaki tree.

14. The aqueous gel of claim 1, wherein the semiochemicals is trimedlure.

15. The aqueous gel of claim 1, wherein the gel further comprises a UV filter.

16. The aqueous gel of claim 1, wherein the thickener is a polysaccharide gum selected from gellan gum, jelutong gum, xanthan gum, guar gum, gum arabic, gum tragacanth, gum karya, tara gum, locust gum, agar agar, carrageenan, alginic acid, and alginates.

17. The aqueous gel of claim 1, wherein the proteins comprise meat meal, fish meal, fish extracts, seafood, seafood extracts, blood meal, insect parts, crickets powder, yeast extracts, egg yolk, protein hydrolysates, yeast autolysates, or gluten hydrolysates.

18. The aqueous gel of claim 1, wherein the dynamic viscosity is in the range from 80 to 500 mPas.

* * * * *